(12) United States Patent
Mottica et al.

(10) Patent No.: US 11,513,062 B2
(45) Date of Patent: Nov. 29, 2022

(54) METHOD FOR CALIBRATING A DEVICE FOR MEASURING THE CONCENTRATION OF A BIOLOGICAL COMPOUND

(71) Applicant: BILIMETRIX S.R.L., Trieste (IT)

(72) Inventors: Matteo Mottica, Trieste (IT); Claudio Tiribelli, Trieste (IT); Carlos Daniel Coda Zabetta, Trieste (IT)

(73) Assignee: BILIMETRIX S.R.L., Trieste (IT)

( * ) Notice: Subject to any disclaimer, the term of this patent is extended or adjusted under 35 U.S.C. 154(b) by 640 days.

(21) Appl. No.: 16/334,927

(22) PCT Filed: Sep. 19, 2017

(86) PCT No.: PCT/IB2017/055657
§ 371 (c)(1),
(2) Date: Mar. 20, 2019

(87) PCT Pub. No.: WO2018/055510
PCT Pub. Date: Mar. 29, 2018

(65) Prior Publication Data
US 2019/0277750 A1   Sep. 12, 2019

(30) Foreign Application Priority Data

Sep. 20, 2016 (IT) .................. 102016000094056

(51) Int. Cl.
*G01N 21/27* (2006.01)
*G01N 21/84* (2006.01)
*G01N 33/72* (2006.01)

(52) U.S. Cl.
CPC ....... *G01N 21/274* (2013.01); *G01N 21/8483* (2013.01); *G01N 33/728* (2013.01); *G01N 2021/8488* (2013.01)

(58) Field of Classification Search
CPC ...... G01N 21/27; G01N 21/274; G01N 33/78; G01N 21/8483; G01N 2021/8494
See application file for complete search history.

(56) References Cited

U.S. PATENT DOCUMENTS

| | | | |
|---|---|---|---|
| 4,852,025 | A | 7/1989 | Herpichobehm et al. |
| 5,795,791 | A | 8/1998 | Hirai et al. |
| (Continued) | | | |

FOREIGN PATENT DOCUMENTS

| | | |
|---|---|---|
| EP | 0353589 | 2/1990 |
| WO | 2012/038930 | 3/2012 |

OTHER PUBLICATIONS

International Search Report cited in PCT/IB2017/055657, dated Jan. 2, 2018.

*Primary Examiner* — Jill A Warden
*Assistant Examiner* — Dwayne K Handy
(74) *Attorney, Agent, or Firm* — Workman Nydegger

(57) ABSTRACT

It is disclosed a method for calibrating an electronic device for measuring the concentration of a biological compound, in particular bilirubin. The method comprises the step a) of performing (10) a plurality of reflectance measurements for each reference strip of a plurality of reference strips (110-1, 110-2, . . . 110-8) having respective predefined concentration values of the biological compound, the step b) of calculating (20), for each reference strip, a respective value of a statistical reflectance indicator as a function of the plurality of reflectance measurements, generating a plurality of values of the statistical reflectance indicator, the step c) of subdividing the plurality of values of the statistical reflectance indicator into at least two subsets (I, II, III), the step d) of interpolating (41) the values of the statistical reflectance indicator of each subset so as to generate an interpolation curve for each subset, the step e) of calculating (43), for each pair of interpolation curves relative to two adjacent subsets (I, II), (Continued)

a reflectance threshold value for which the difference of the reflectance values of the pair of interpolation curves is minimum, the step f) of selecting, for each interpolation curve, a portion delimited at least in part by the respective reflectance threshold values, said portion being associated with the respective plurality of values of the statistical reference indicator, and the step g) of generating (50) a calibration curve of the electronic device by combining the selected portions of the interpolation curves.

14 Claims, 4 Drawing Sheets

(56) References Cited

U.S. PATENT DOCUMENTS

| | | | |
|---|---|---|---|
| 2007/0273928 A1 | 11/2007 | Robinson et al. | |
| 2015/0286778 A1* | 10/2015 | Aigner | G16B 40/10 |
| | | | 436/70 |
| 2015/0308961 A1 | 10/2015 | Burg et al. | |
| 2019/0128907 A1* | 5/2019 | Tahara | G01N 21/274 |

\* cited by examiner

METHOD FOR CALIBRATING A DEVICE FOR MEASURING THE CONCENTRATION OF A BIOLOGICAL COMPOUND

TECHNICAL FIELD OF THE INVENTION

The present invention concerns the field of medical devices.

In particular, the present invention relates to a method for calibrating a device for measuring the concentration of bilirubin in blood.

PRIOR ART

Bilirubin is a molecule produced by the catabolic processes of haemoglobin mainly caused by the destruction of senescent red blood cells.

The high antioxidant activity of bilirubin has led to the hypothesis that this molecule mainly performs a cellular antioxidant function.

However, in situations in which too much haemoglobin is degraded or malfunctioning arises in the disposal mechanisms, bilirubin can accumulate in the blood causing jaundice, with posterior deposit thereof in the tissues. In fact, the increase in concentration of bilirubin in the blood is highlighted by the yellowish colouring of the skin, sclera and mucosa.

Jaundice is common in neonates and arises because after the birth the neonate starts to use red blood cells containing molecules of haemoglobin suitable for extrauterine life, leading to the disposal of the red blood cells with foetal haemoglobin belonging to intrauterine life. As a consequence of this, during the first days of life, a large quantity of red blood cells with foetal haemoglobin are degraded and, in addition to the fact that the liver of the neonate responsible for disposing of the bilirubin is not yet operating at its maximum level, a large quantity of bilirubin is produced and accumulates in the blood.

Despite jaundice being a physiological condition in most cases, it must not be underestimated as it can have serious effects on the infant's health. The blood-brain barrier in neonates is not yet appropriately formed and if a concentration of 25 mg/dL is exceeded, the bilirubin starts to be deposited in the cerebral tissue causing brain damage (kernicterus).

Diseases generated by excess bilirubin are among the main causes of long term disabilities in children born in developing countries. This is partly due to the presence of genetic risk factors (e.g. glucose-6-phosphate dehydrogenase deficiency (G6PD)), but mainly to the limited economic and structural resources that prevent the suitable management of the diagnosis and therapy of neonatal jaundice.

In fact, it is extremely important to monitor the level of bilirubin in neonates to determine whether it is necessary to initiate appropriate therapies (e.g. phototherapy) that facilitate the disposal of any excess.

Current practice envisages monitoring the bilirubin concentration level before discharging the child from the hospital; this routine test is performed in laboratories exploiting methods based on chemical reactions that produce coloured compounds that can be measured spectroscopically by analysing a blood sample normally obtained by taking a blood sample from the neonate's heel.

Over recent years, measuring tools have been developed to allow the analysis of the concentration of bilirubin in a non-invasive way.

A transcutaneous reflectometer (BiliCheck®, Respironics Inc.) is known, for example, that estimates the concentration of bilirubin based on the intensity of the yellow colouring of the skin. As well as not being invasive, it also allows accurate measurements to be obtained up to concentration levels of about 15 mg/dL.

However, this type of measurement still has drawbacks and disadvantages, mainly:
limited accuracy for high concentration level measurements, for example above 15 mg/dL;
limited measurement scale with maximum measurable value of 20 mg/dL;
limited accuracy in neonates with non-Caucasian complexion.

Patent WO 2012/038930 is also known, which discloses a method and related device for measuring bilirubin.

In particular, WO 2012/038930 discloses a method for determining a calibration curve that has the disadvantage of being less accurate as the bilirubin concentration value to be measured increases: in this way, for high bilirubin levels, which are those of greatest interest as they are the ones used to determine whether therapy needs to be prescribed or not, the accuracy decreases, hence increasing the risk of obtaining an incorrect and unreliable concentration measurement. This unreliability is motivated by the fact that the reference strips described for obtaining the calibration curve do not guarantee reproducibility during industrial production, which has a direct impact on the resulting calibration accuracy of the measurement device.

US 2015/308961 discloses a system for calibrating a portable electronic device based on the use of a diagnostic tool comprising a reference colour from which a digital image is captured by a digital camera that is part of the electronic device; the latter is used in turn to capture a digital image of the colour changes resulting from a chemical reaction of a biological compound of interest with a specific reagent, to then be compared with the digital image of the reference colour and to determine the concentration of the biological compound.

U.S. Pat. No. 5,795,791 relates to the quantitative analysis of liquid samples based on optical measuring techniques and discloses that a sigmoid calibration curve is split into three areas of increasing concentration, wherein the calibration curve of each area is approximated by a respective interpolation function, so that two adjacent curves are connected in the point in which they have the same slope.

BRIEF SUMMARY OF THE INVENTION

Therefore it is an object of the present invention to provide a calibration method for an opto-electronic device for measuring the concentration of biological compounds (for example, bilirubin) that allows to overcome the limitations of the prior art.

In particular, it is an object of the present invention to provide a calibration method for measuring the concentration of bilirubin which allows a high accuracy of measurements to be obtained, also for high bilirubin concentration values, reducing, for example, the error below a 5% threshold.

It is also an object of the present invention to provide a simple calibration method, efficient from the computational point of view and also easy to use in developing countries.

It is also an object of the present invention to provide a robust calibration method over time, i.e. that is reproducible at industrial level with accuracy.

The specified technical task and the specified aims are substantially achieved by a method for calibrating an opto-electronic device to measure the concentration of biological compounds (e.g. bilirubin).

The dependent claims correspond to different possible or preferred embodiments of the invention.

In particular, the calibration method according to the present invention envisages to perform various reflectance measurements on a plurality of reference strips corresponding to predefined bilirubin concentration values (i.e. known); subsequently, the values of a statistical indicator are calculated (e.g. the mean reflectance values) obtained from the measurements performed on the individual reference strips.

The calibration method is characterised by subdividing the obtained values of the statistical indicator into at least two subsets and by interpolating the values of the statistical reflectance indicator of each subset so as generate an interpolation curve for each subset.

Then, for each pair of interpolation curves relating to two adjacent subsets, a threshold reflectance value is calculated for which the difference of the reflectance values of the pair of interpolation curves is minimum.

Then, for each interpolation curve, a portion delimited at least in part by the respective threshold reflectance values is selected, said portion being associated with the respective plurality of values of the statistical reflectance indicator.

Finally, a calibration curve of the opto-electronic device is generated by combining the selected portions of the interpolation curves.

According to a further aspect of the invention, the calibration method comprises the use of reference strips for calibrating any opto-electronic device for measuring biological compounds (e.g. to measure the concentration of bilirubin or haemoglobin), wherein the reflectance difference between the different reference strips composing a calibration set of the measuring device is determined by different dichromatic textures formed by one or more types of patterns, which vary in the percentage of pixels for both colours and are repeated sequentially to form the dichromatic textures.

In particular, reference strips are used formed by dichromatic textures composed of patterns having black and white pixels, for the purpose of adjusting the intensity of the light beam reflected by each reference strip, at any given wavelength, to perform the calibration of the device for measuring the concentration of biological compounds: in this way the reflected light detected by the optical sensor of the measuring device performing the calibration method is provided exclusively by the white surface exposed by the white pixels.

By increasing the percentage of white pixels with respect to that of the black pixels in the different patterns forming the different dichromatic textures of the different reference strips, the quantity of reflected light increases, hence creating a plurality of reference strips that represent respective known concentrations of the values of the measured compound, such as for example bilirubin.

Advantageously, when the dichromatic reference strips are irradiated with a monochromatic optical beam at a specific wavelength, the reflected optical beam will have the same wavelength, hence guaranteeing the accuracy of the calibration of the opto-electronic device performing the measure of the concentration of the analysed biological compound, such as for example bilirubin.

BRIEF DESCRIPTION OF THE DRAWINGS

Further characteristics and advantages of the present invention will appear more clearly from the indicative and thus non-limiting description of a preferred, but not exclusive, embodiment of a method for calibrating devices for measuring the concentration of a biological compound, such a, for example the concentration of bilirubin in a blood sample.

This description will be set out below with reference to the attached drawings, provided solely for indicative and thus non-limiting purposes, in which.

DETAILED DESCRIPTION OF THE INVENTION

Figure 1:
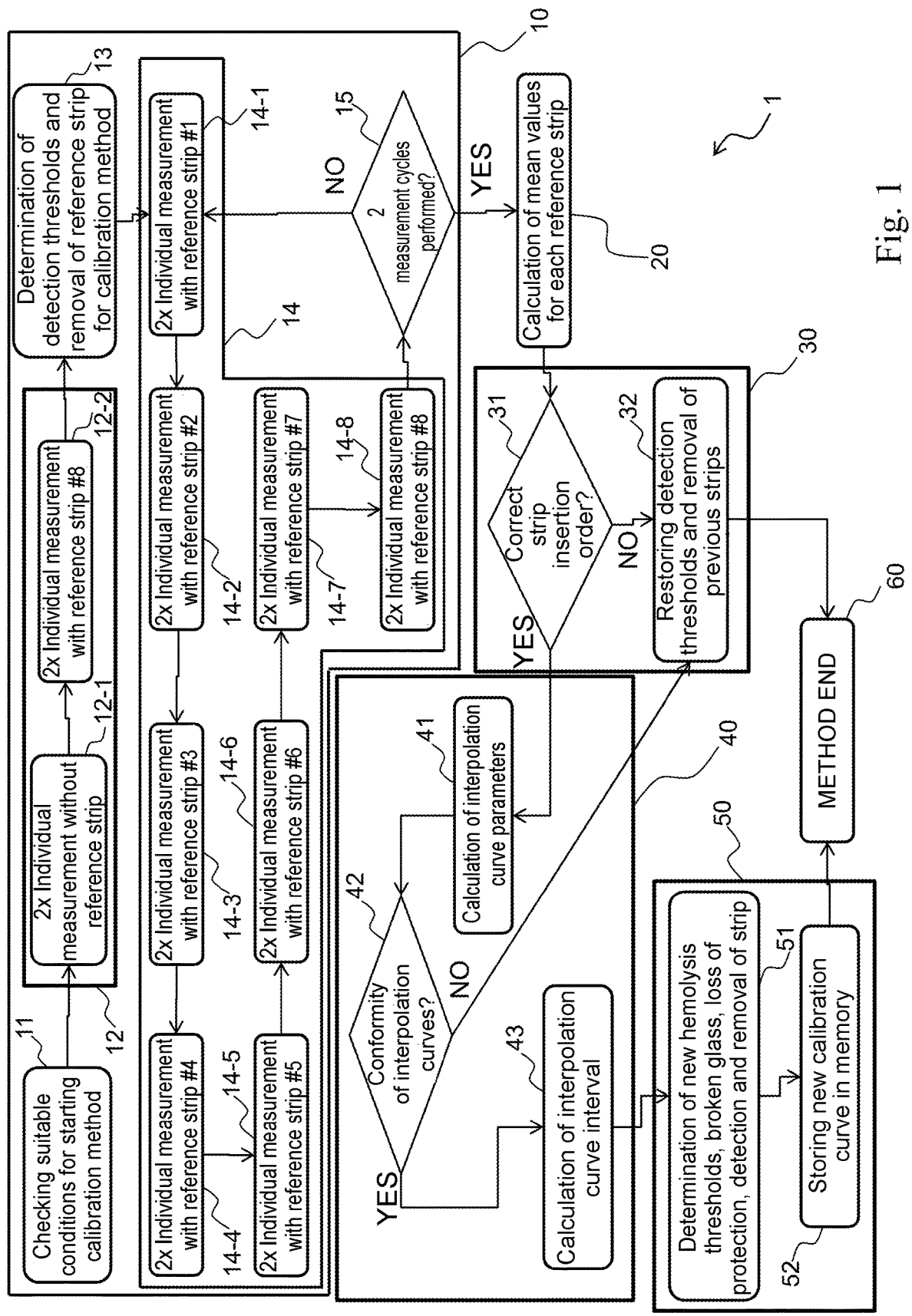
FIG. 1 shows the flow diagram of the calibration method according to the invention implemented on an opto-electronic device for measuring the concentration of a biological compound.

FIG. 1 shows, by way of example, the flow diagram 1 representing in detail the steps of the calibration method according to the invention.

The calibration method is performed on a processing unit (e.g. a microprocessor) mounted inside a portable opto-electronic device, which performs the measure of the concentration of a biological compound (e.g. concentration of bilirubin in blood samples), using a plurality of reference strips corresponding to predefined (i.e. known) concentration values of the biological compound (e.g. bilirubin).

For the purpose of explaining the flow diagram 1, for simplicity it is considered that the biological sample is a blood sample and that the calibration method is used for a device for measuring the concentration of bilirubin.

Reference number 10 indicates the step of measuring the reference strips corresponding to known bilirubin concentration values.

For the purposes of explaining the invention, a particular embodiment has been considered in FIG. 1 wherein an optimal number of reference strips equal to eight has been chosen.

For each reference strip, a plurality of measurements are performed; in particular, for the embodiment described herein by way of non-limiting example, four measurements are performed, subdivided into two successive cycles each one comprising two measurements.

The measuring step 10 starts with the control step 11 in which it is checked that the electronic measuring device is operating correctly.

From step 11 you continue to step 12 in which a pair of double measurements are performed, the first in step 12-1 without inserting any reference strips into the electronic device for determining the minimum reflectance value in the absence of inserted reference strips, the second in step 12-2 it is performed with the reference strip corresponding to the maximum predefined bilirubin concentration value to determine the minimum reflectance value in the presence of inserted reference strips.

From step 12 you continue to step 13 in which, based on the reflectance values obtained in step 12, the identification thresholds are determined for the insertion and removal of the reference strips relating to the calibration step of the electronic device.

The term identification threshold for the insertion and removal of the reference strips means the minimum and the maximum reflectance value indicating the presence of a reference strip within the unit of measurement of the optoelectronic device.

Such thresholds, functional to the calibration method, are then recalculated correctly using the values of the statistical indicator obtained during step 51 that will be discussed in more detail below.

From step 13 you continue to a first cycle of measurements 14 performing two reflectance measurements for each one of the available eight reference strips that are inserted into the electronic device following for example an increasing order of the predefined concentration level of bilirubin to which they correspond.

In particular, the following steps are performed in the order:

step 14-1 in which the first reference strip is inserted and two reflectance measurements are performed on the first reference strip;

step 14-2 in which the second reference strip is inserted corresponding to a higher predefined concentration of bilirubin than that of the first reference strip and two reflectance measurements are performed on the second reference strip;

step 14-3 in which the third reference strip is inserted corresponding to a higher predefined concentration of bilirubin than that of the second reference strip and two reflectance measurements are performed on the third reference strip;

step 14-4 in which the fourth reference strip is inserted corresponding to a higher predefined concentration of bilirubin than that of the third reference strip and two reflectance measurements are performed on the fourth reference strip;

step 14-5 in which the fifth reference strip is inserted corresponding to a higher predefined concentration of bilirubin than that of the fourth reference strip and two reflectance measurements are performed on the fifth reference strip;

step 14-6 in which the sixth reference strip is inserted corresponding to a higher predefined concentration of bilirubin than that of the fifth reference strip and two reflectance measurements are performed on the sixth reference strip;

step 14-7 in which the seventh reference strip is inserted corresponding to a higher predefined concentration of bilirubin than that of the sixth reference strip and two reflectance measurements are performed on the seventh reference strip;

step 14-8 in which the eighth reference strip is inserted corresponding to a higher predefined concentration of bilirubin than that of the seventh reference strip and two reflectance measurements are performed on the eighth reference strip.

Therefore the reference strips are numbered from one to eight according to an increasing concentration of bilirubin.

It is possible to provide other measurement procedures that follow a predefined measurement order of the reference strips, different from the one chosen for this particular embodiment.

For example, according to a further possible embodiment, the reflectance measurements could be performed by inserting the reference strips into the electronic device according to a decreasing or alternating order of the predefined bilirubin concentration level to which they correspond.

This first cycle of measurements 14 is performed twice.

Advantageously, according to a further aspect of the invention, in the first cycle of measurements 14 composed of eight steps eight reference strips are used, each one formed by images having dichromatic textures, i.e. images composed of pixels having two monochromatic components, in which, between successive dichromatic textures associated with the reference strips, the ratio is varied between the percentage of pixels of the two monochromatic components, as shown schematically in the dichromatic textures 110-1, 110-2, 110-3, 110-4, 110-5, 110-6, 110-7, 110-8 shown in the lower part of FIG. 3: in this way, the calibration is performed using the reflectance difference between different reference strips, independently from the frequency of the optical beam source used to measure the concentration of the biological compound.

More in particular:

in step 14-1 the first reference strip having the first dichromatic texture 110-1 is inserted into the electronic device;

in step 14-2 the second reference strip having the second dichromatic texture 110-2 is inserted into the electronic device;

in step 14-3 the third reference strip having the third dichromatic texture 110-3 is inserted into the electronic device;

in step 14-4 the fourth reference strip having the fourth dichromatic texture 110-4 is inserted into the electronic device;

in step 14-5 the fifth reference strip having the fifth dichromatic texture 110-5 is inserted into the electronic device;

in step 14-6 the sixth reference strip having the sixth dichromatic texture 110-6 is inserted into the electronic device;

in step 14-7 the seventh reference strip having the seventh dichromatic texture 110-7 is inserted into the electronic device;

in step 14-8 the eighth reference strip having the eighth dichromatic texture 110-8 is inserted into the electronic device;

In steps 14-1, 14-2, . . . 14-8 an increasing order of the bilirubin concentration value is used, i.e. the dichromatic texture 110-1 of the first reference strip corresponds to the minimum concentration of bilirubin, the dichromatic texture 110-2 of the second reference strip corresponds to a higher concentration of bilirubin than that of the dichromatic texture 110-1 of the first reference strip, the dichromatic texture 110-3 of the third reference strip corresponds to a higher concentration of bilirubin than that of the dichromatic texture 110-2 of the second reference strip, . . . and so on until the dichromatic texture 110-8 of the eighth reference strip that corresponds to the maximum concentration of bilirubin.

Alternatively, it is possible to use a decreasing or alternating order of the bilirubin concentration value.

It is to be observed that the use of calibration strips made of dichromatic textures allows to obtain a calibration which is maintained robust over time and which can be reproduced with accuracy in industrial production, since the ratio between the overall luminance of different calibration strips is maintained substantially constant over time.

Differently, WO 2012/038930 discloses the use of reference strips for calculating the calibration curve that are made of coloured inks whose composition could vary over time, reaching variations in the reference colour for a specific bilirubin concentration value: in this way, the reproducibility of the reference strips in industrial production is not guaranteed, with the consequence of reducing the calibration accuracy of the bilirubin concentration measurement device.

Preferably, the eight dichromatic textures 110-1, 110-2, . . . 110-8 are composed of black and white pixels, as shown in the lower part of FIG. 3: in this case, it is possible to observe that the percentage of black and white pixels varies between two successive dichromatic textures.

For example:
- in the texture 110-1 of the first reference strip the percentage of white pixels is maximum, thus the percentage of black pixels is minimum;
- the percentage of white pixels decreases between the texture 110-1 of the first reference strip and the texture 110-2 of the second reference strip (thus the percentage of black pixels increases);
- the percentage of white pixels decreases between the texture 110-2 of the second reference strip and the texture 110-3 of the third reference strip (thus the percentage of black pixels increases);
- this difference in pixels between the reference strips is repeated until the texture 110-8 of the eighth reference strip in which the percentage of white pixels is minimum, therefore the percentage of black pixels is maximum.

The textures 110-1, 110-2, . . . 110-8 formed by black and white pixels differ due to the percentage of black and white pixels: in this way, the resulting white surface, when illuminated by a light source at a specific wavelength for performing the calibration of the opto-electronic device for measuring the concentration of a biological compound, varies from one reference strip to another, allowing eight reference strips to be created that represent known concentrations of the biological compound analysed (e.g. bilirubin) and allowing the reflected light beam to be varied (also proportionally).

It is observed that two-colour combinations different than the used black and white are possible for the textures to detect the concentration of bilirubin; for example, it is possible to use for the reference strips a plurality of dichromatic textures composed of white and yellow pixels to detect the concentration of bilirubin, or white and red to detect the concentration of haemoglobin.

Preferably, the eight dichromatic textures 110-1, 110-2, . . . 110-8 associated with the eight reference strips are formed by means of the repetition of the same dichromatic image of a pattern 100-1, 100-2, 100-3, 100-4, 100-5, 100-6, 100-7, 100-8; alternatively, the eight dichromatic textures 110-1, 110-2, 110-3, 110-4, 110-5, 110-6, 110-7, 110-8 are formed by means of the combination of two or more dichromatic images of patterns 100-1, 100-2, 100-3, 100-4, 100-5, 100-6, 100-7, 100-8.

Figure 3A:
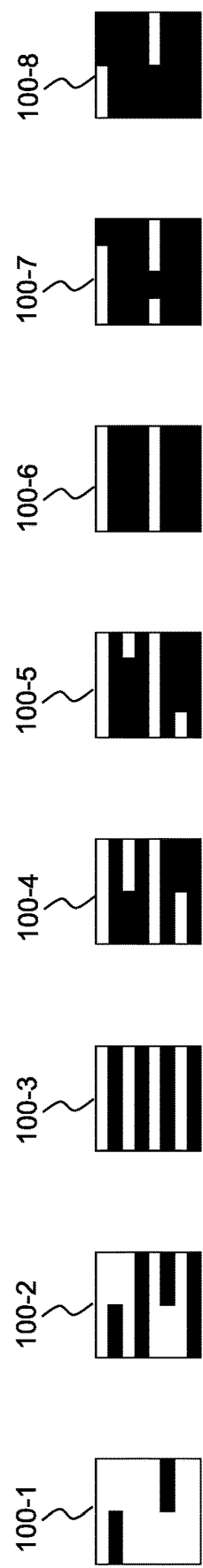
FIG. 3A shows eight possible black and white pixel configurations that form eight possible image patterns.
Figure 3B:
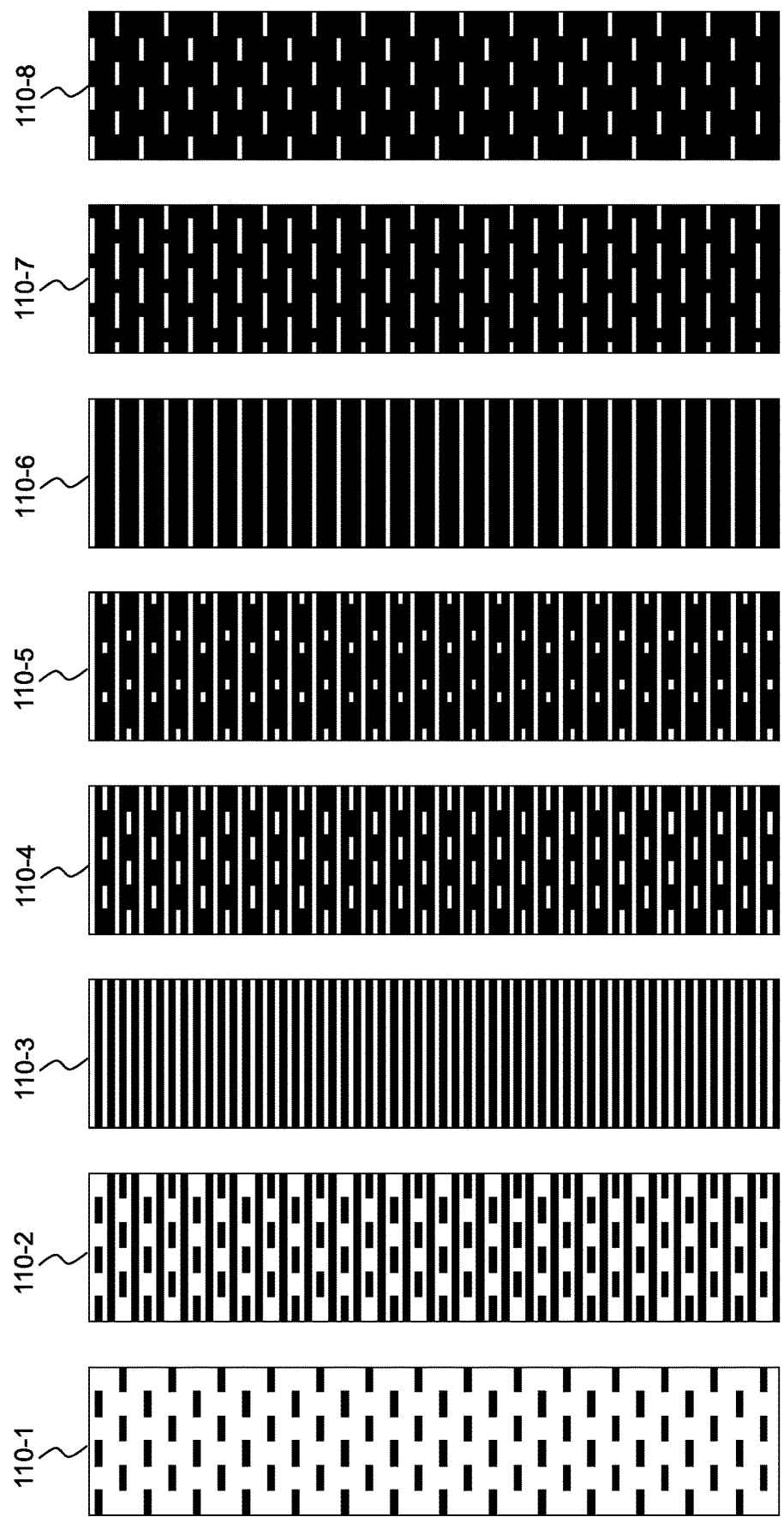
FIG. 3B shows eight possible respective dichromatic textures of eight reference strips generated by the eight image patterns for creating eight reference strips.

For example, FIG. 3A shows eight possible patterns 100-1, 100-2, 100-3, 100-4, 100-5, 100-6, 100-7, 100-8 of images formed by 8×8 black and white pixels; by means of the repetition of the same pattern of the image the eight dichromatic textures are created 110-1, 110-2, 110-3, 110-4, 110-5, 110-6, 110-7, 110-8 shown in FIG. 3B, which define the different reference strips for the calibration of the opto-electronic device for measuring the concentration of biological compound (e.g., bilirubin).

More in particular:
- the texture 110-1 of black and white pixels is formed by means of the repetition of the pattern 100-1 three times in the horizontal direction (with respect to the reading direction of FIG. 3) and the repetition of the pattern 100-1 thirteen times in the vertical direction (with respect to the reading direction of FIG. 3) for each of the three times of the horizontal direction, so as to form a matrix composed of 14 rows and 3 columns, in which each element of the 14×3 matrix is composed of the pattern 100-1 of the image of black and white pixels;
- the texture 110-2 of black and white pixels is formed by means of the repetition of the pattern 100-2 three times in the horizontal direction and the repetition of the pattern 100-2 thirteen times in the vertical direction for each of the three times of the horizontal direction, so as to form a matrix composed of 14 rows and 3 columns, in which each element of the 14×3 matrix is composed of the pattern 100-2 of the image of black and white pixels;
- and so on until the texture 110-8 of black and white pixels is formed by means of the repetition of the pattern 100-8 three times in the horizontal direction and the repetition of the pattern 100-8 thirteen times in the direction for each of the three times of the horizontal direction, so as to form a matrix composed of 14 rows and 3 columns, in which each element of the 14×3 matrix is composed of the pattern 100-8 of the image of black and white pixels.

Alternatively, one or more of the textures 110-1, 110-2, . . . 110-8 of black and white pixels is formed by means of the repetition of a combination of two of the patterns 100-1, 100-2, . . . 100-8; for example, the texture 110-1 is formed by the repetition of a combination of the patterns 100-1 and 100-2.

The different textures 110-1, 110-2, . . . 110-8 created respectively by the patterns 100-1, 100-2, . . . 100-8 consequently differ in the percentage of black and white pixels: in this way, the resulting white surface, when illuminated by a light source for performing the calibration of the opto-electronic device for measuring biological samples, varies from one reference strip to another, allowing eight reference strips to be created that represent known concentrations of the biological compound analysed (e.g. bilirubin).

From step 14-8 (i.e. at the end of the first cycle 14) you continue to step 15 wherein it is checked whether two measurement cycles 14 have been performed:
- in the positive case (i.e. two measurement cycles 14 have been performed), from step 15 you continue to step 20 wherein, for each individual reference strip, a statistical indicator is calculated as a function of the reflectance values acquired during the measurement step 10: in this way for each known bilirubin concentration value a calculated reflectance value is obtained, which is as reliable as possible, being the average of various values measured so as to minimise the statistical error.

Preferably, said statistical indicator is selected from one of the following list:
mean;
mode;
median.

Preferably, from step 20 you continue to step 30 wherein it is checked whether the reference strips have been measured according to the correct order.

In particular, from step 20 you continue to step 31 wherein it is checked whether the reference strips have been measured according to the correct order (i.e. the values of the statistical reflectance indicator of the reference strips ordered from one to eight must all be decreasing):

in the negative case, from step 31 you continue to step 32 wherein the values of the detection thresholds are restored and the previous strips are removed, thus the flow diagram 1 finishes;

in the positive case, from step 31 you continue to step 40 wherein the values of the statistical reflectance indicator obtained through the previous steps are interpolated.

In particular, step 40 comprises step 41 wherein the calculated values of the statistical reflectance indicator are subdivided into a plurality of subsets.

Figure 2:
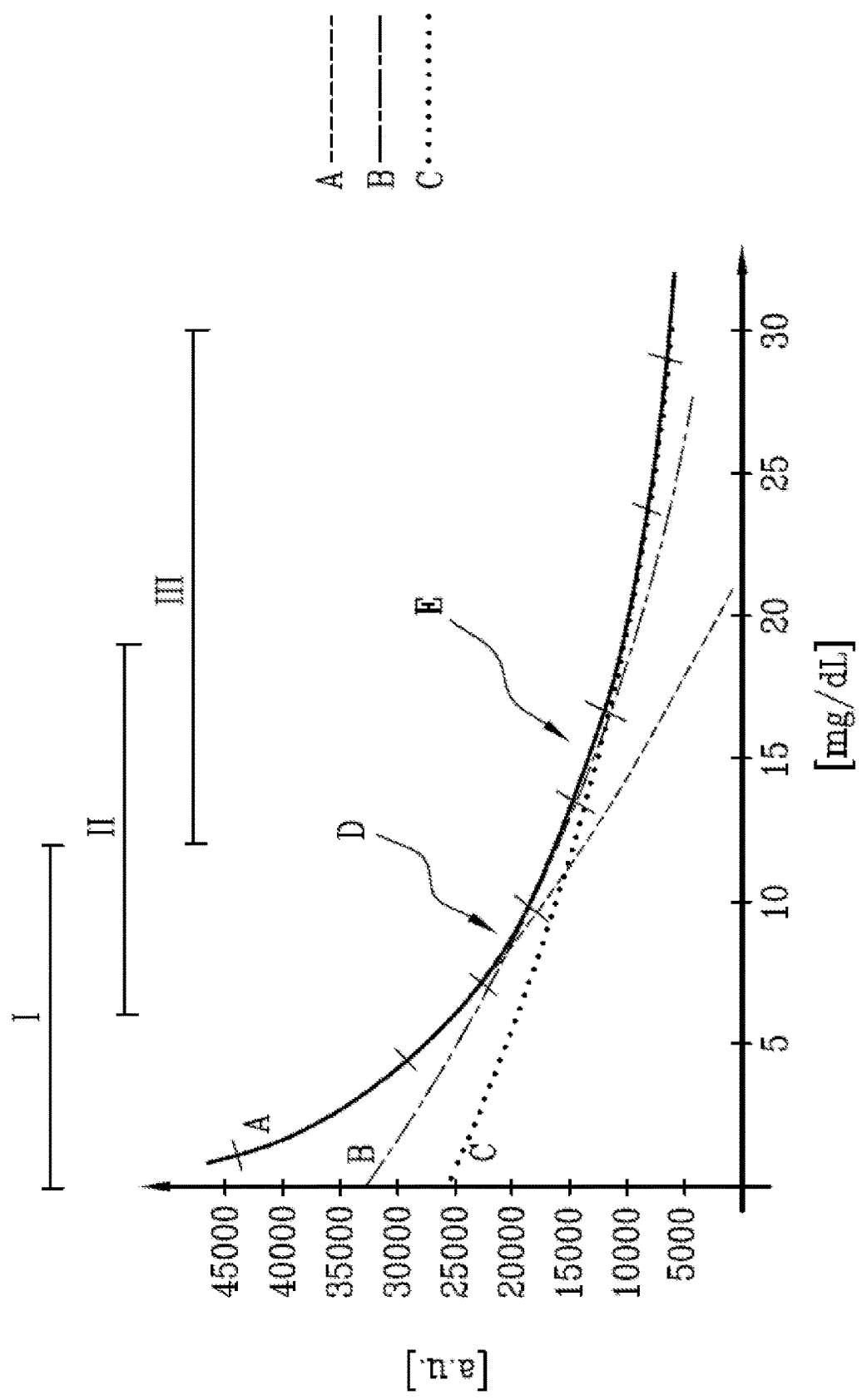
FIG. 2 shows a possible trend of a calibration curve obtained according to the method of the invention.

Preferably, with reference to FIG. 2, the values of the statistical reflectance indicator are subdivided into three subsets I, II, II, each one composed of four consecutive values, and then in step 41 the parameters of three interpolation curves "A", "B", "C" are calculated so that:

the values of the statistical reflectance indicator obtained from the measurements performed on the first, second, third and fourth reference strip belonging to the first subset I are interpolated to obtain a first interpolation curve "A" (indicated with a dashed curve in FIG. 2);

the values of the statistical reflectance indicator obtained from the measurements performed on the third, fourth, fifth and sixth reference strip belonging to the second subset II are interpolated to obtain a second interpolation curve "B" (indicated with a dashed-dotted curve in FIG. 2);

the values of the statistical reflectance indicator obtained from the measurements performed on the fifth, sixth, seventh and eighth reference strip belonging to the third subset III are interpolated to obtain a third interpolation curve "C" (indicated with a dotted curve in FIG. 2).

From step 41 you continue to step 42 wherein the conformity of the three interpolation curves obtained is checked.

For example, to assess the conformity of the curves, for each reference strip, the bilirubin concentration values are calculated obtained based on the value of the statistical reflectance indicator using the interpolation curves to which they pertain.

In the considered case wherein three interpolation curves were obtained, in step 42 the following are calculated:

with the interpolation curve "A" the concentrations of bilirubin of the statistical reflectance indicator of the first, second, third and fourth reference strip;

with the interpolation curve "B" the concentrations of bilirubin of the statistical reflectance indicator of the third, fourth, fifth and sixth reference strip;

with the interpolation curve "C" the concentrations of bilirubin of the statistical reflectance indicator of the fifth, sixth, seventh and eighth reference strip.

To check the conformity, the difference is calculated, ideally equal to zero, between the value of bilirubin calculated and the predefined value of bilirubin of each reference strip.

The conformity check of an interpolation curve is passed with a positive outcome if the differences of each bilirubin value calculated with it and the corresponding predefined bilirubin value all fall within predefined intervals (e.g.: predefined bilirubin value ±5% or predefined bilirubin value ±0.5 mg/dL).

If the check in step 42 has a negative outcome, after step 42 it is necessary to return to the previous step 32.

In the event that the check in step 42 has a positive outcome, from step 42 you continue to step 43 wherein the interval of the interpolation curves "A", "B", "C" is calculated.

In particular, the reflectance threshold values are calculated as bilirubin concentration values that correspond to a minimum difference, ideally equal to zero, in terms of reflectance measurement value, between two interpolation curves relating to adjacent subsets.

In the considered case in which three interpolation curves were obtained, in step 43 it is calculated:

a first reflectance threshold value "D" corresponding to the minimum difference between the first interpolation curve "A" and the second interpolation curve "B";

a second reflectance threshold value "E" corresponding to the minimum difference between the second interpolation curve "B" and the third interpolation curve "C";

Subsequently, for each interpolation curve "A", "B", "C", a portion is selected, delimited at least in part by the respective reflectance threshold values.

Considering again the case of three interpolation curves, the following portions are selected:

a portion of the interpolation curve "A" comprised between the maximum reflectance value measurable and the first reflectance threshold value "D";

a portion of the interpolation curve "B" comprised between the first reflectance threshold value "D" and the second reflectance threshold value "E";

a portion of the interpolation curve "C" comprised between the second reflectance threshold value "E" and the minimum measurable reflectance value.

Finally, a calibration curve of the electronic device is generated as the curve resulting from the combination of the three selected portions of the interpolation curves.

It is observed that the reflectance thresholds ("D", "E") are those in which the difference of the values between the two considered interpolation curves ("A"-"B" for threshold D, "B"-"C" for threshold E) is minimum, therefore in the connection points between two adjacent interpolation curves no constraint is used relating to the same slope (first derivative), which can thus be different: in this way, an optimal trend of the interpolation curves is selected (e.g. curves "A" and "B") in the final part (i.e. in the final part of the curve "A" from the side adjoining the curve "B" and in the final part of the curve "B" from the side adjoining the curve "A").

For example, it is possible that in the connection point between two adjacent interpolation curves (e.g. between "A" and "B") it is present a non-linearity (for example, a cusp or a step between two different values) and thus the overall trend of the resulting calibration curve is not uniform: in this way it is possible to take into account the non-linear behaviour of the opto-electronic source (e.g. an LED) used in the measurement device using the calibration curve generated according to the invention and it is possible to take into account the behaviour of digital components present inside the measurement device.

Differently, U.S. Pat. No. 5,795,791 discloses that two adjacent interpolation curves are connected in the point in which they have the same slope, so as to have a uniform trend of the resulting calibration curve, i.e. the criterion of the same slope is used as priority: in this way it is possible that it is not selected an optimal trend of the interpolation curves in the final part.

Advantageously, from step 43 you continue to step 50 wherein new control threshold values are defined, as a function of the calibration curve generated by the previous steps, for example detection of hemolysis presence in the sample, damage to the measurement unit and loss of protection of the optical sensor. These allow to immediately identify a series of problems that can jeopardise the correct operation of the electronic device or make the measurement inaccurate. For example, a reflectance value extremely below the normal scale values could indicate damage to the measurement unit that makes the instrument unusable.

From step 51 you continue to step 52 wherein the obtained calibration curve is stored (into a memory inside the electronic measurement device) and the flow diagram 1 terminates with step 60.

According to the preferred embodiment, eight reference strips are used for which the measured reflectance values are subdivided into three subsets I, II, III, as shown in FIG. 2 representing the trend of the calibration curve of the electronic device and of the interpolation curves used to generate it.

In particular:
"A" indicates the first interpolation curve obtained by interpolating the statistical indicator values (foe example, the means of the values) measured with the first four reference strips, i.e. those from the first to the fourth included;
"B" indicates the second interpolation curve obtained by interpolating the statistical indicator values (in the example, the means of the values) measured with the 4 intermediate reference strips, i.e. those from the third to the sixth included;
"C" indicates the third interpolation curve obtained by interpolating the statistical indicator values (in the example, the means of the values) measured with the last four reference strips, i.e. those from the fifth to the eighth included.

The proximity of the bilirubin concentration values of the reference strips that form the interpolation curve "B", i.e. the one which contributes to the definition of the central portion of the calibration curve, is greater with respect to the proximity of the bilirubin concentration values of the reference strips in the lateral portions of the calibration curve, defined by the contributions provided by the interpolation curves "A" and "C": this advantageously allows a further improvement to be obtained in the accuracy of the calibration method in the central portion of the calibration curve, this part being very important from a clinical point of view for diagnosing neonatal jaundice that is dangerous to the health of the neonate and determine whether it is necessary or not to initiate the appropriate therapies.

The points relating to the reflectance thresholds that determine the change between the interpolation curves "A", "B" and "C" have been indicated respectively as:
"D": point of the reflectance threshold value corresponding to the minimum distance between the first curve "A" and the second curve "B";
"E": point of the reflectance threshold value corresponding to the minimum distance between the second curve "B" and the third curve "C".

Therefore the calibration curve of the electronic device will be the curve constructed considering the contributions of the individual interpolation curves obtained by selecting the portion of interpolation curve according to the above described steps combined as follows:
for measured reflectance values that are higher than the reflectance value corresponding to the reflectance threshold value "D", the first interpolation curve "A" is used;
for measured reflectance values comprised between the reflectance threshold value "D" and the reflectance threshold value "E", the second interpolation curve "B" is used;
for measured reflectance values that are lower than the reflectance value corresponding to the reflectance threshold value "E", the third interpolation curve "C" is used.

Considering the contributions obtained by specific interpolation curves for each interval of measurable values of bilirubin concentration, a calibration curve is constructed for the electronic device that allows the accuracy of the result to be improved since for every interval the portion of used interpolation curve is that which best approximates the measurable values in that particular interval, consequently reducing the error.

Advantageously, the method according to the present invention allows high accuracy to be obtained in the measurement of the bilirubin concentration values also calibrating the electronic device with a relatively limited number of reference strips (e.g. eight).

It is also an object of the present invention a portable opto-electronic device to measure the concentration of a biological compound such as, for example, bilirubin of a blood sample.

The opto-electronic device comprises an optical source configured to emit an incident optical beam on the biological sample (e.g. a blood sample) on an absorption strip.

The opto-electronic device further comprises at least one photo-detector configured to detect an optical beam reflected by the biological sample.

The opto-electronic device further comprises a processing unit (e.g. a microprocessor) electrically connected with the optical source and with the photo-detector, wherein said processing unit is configured to perform the steps of the above-described calibration method according to the invention.

The processing unit further has the function of performing measurements of biological samples (e.g. the concentration of bilirubin on a blood sample) by means of the reflectance measurement of the optical beam reflected by the biological sample.

The optical source is for example formed by one or more light-emitting diodes (e.g. six) that emit optical beams, having for example two wavelengths.

The photo-detector is for example a photo-diode.

The invention claimed is:
1. A method for generating a calibration curve for an opto-electronic device for measuring a concentration of a biological compound, the method comprising:
 a) performing a reflectance measurement for each reference strip of a plurality of reference strips to obtain a plurality of reflectance measurements, the plurality of reference strips having respective predefined concentration values of the biological compound;
 b) calculating, for each reference strip, a respective value of a statistical reflectance indicator as a function of the plurality of reflectance measurements, and generating a plurality of values of the statistical reflectance indicator,
 c) subdividing the plurality of values of the statistical reflectance indicator into at least two subsets;
 d) interpolating the values of the statistical reflectance indicator of each subset and generating an interpolation curve for each subset in the at least two subsets;
 e) calculating, for each pair of interpolation curves relating to two adjacent subsets, a threshold reflectance value for which a difference of the reflectance values of the pair of interpolation curves is minimum;
 f) selecting, for each interpolation curve, a portion delimited at least in part by the respective threshold reflec- tance values, said portion being associated with the respective plurality of values of the statistical reflectance indicator;

g) generating a calibration curve of the opto-electronic device by combining the portion selected from each of the interpolation curves.

2. The method according to claim 1, further comprising, before step a), the step of providing said plurality of reference strips, wherein:
 each reference strip comprises a dichromatic texture composed of pixels having two monochromatic components;
 the dichromatic textures of each pair of reference strips, selected from the plurality of reference strips, differ for the percentage of pixels of the two monochromatic components.

3. The method according to claim 2, wherein the step of providing the plurality of reference strips comprises:
 providing a plurality of dichromatic images of patterns;
 forming each dichromatic texture, of the plurality of reference strips, by means of the repetition of at least one of the patterns of the dichromatic images.

4. The method according to claim 2, wherein the two monochromatic components are black and white.

5. The method according to claim 1, wherein two adjacent subsets partially overlap.

6. The method according to claim 1, wherein the distance between the predefined concentration values of the biological compound of the reference strips is less in a part of the reflectance measurement interval between two further parts of the reflectance measurement interval.

7. The method according to claim 1, wherein the order in which the plurality of reference strips is measured determines a measurement cycle that follows an ascending or descending order of the concentration of the biological compound, and wherein observance of said order is verified after having calculated the plurality of values of the statistical reflectance indicator.

8. The method according to claim 1, wherein the plurality of reflectance measurements is performed by carrying out a plurality of measurement cycles, in each of which every reference strip is measured two or more times.

9. The method according to claim 1, wherein each subset is composed of the values of the statistical reflectance indicator obtained from measurements performed on reference strips relating to contiguous concentration values of the biological compound.

10. The method according to claim 1, wherein the number of reference strips used for performing the reflectance measurements is equal to eight.

11. The method according to claim 9, wherein each subset is composed of four values of the statistical reflectance indicator obtained from measurements performed on reference strips relating to contiguous concentration values of the biological compound.

12. The method according to claim 1, wherein the plurality of values of the statistical reflectance indicator are selected from one of the following list:
 a plurality of mean reflectance values;
 a plurality of mode reflectance values;
 a plurality of median reflectance values.

13. The method according to claim 1, wherein the plurality of values of the statistical reflectance indicator are a plurality of mean reflectance values,
 and wherein the plurality of mean reflectance values is subdivided into three subsets according to the following criterion:
  the mean values obtained from the measurements performed on the first four reference strips form the first subset;
  the mean values obtained from the measurements performed on the reference strips from the third to the sixth form the second subset;
  the mean values obtained from the measurements performed on the reference strips from the fifth to the eighth form the third subset.

14. The method according to claim 1, wherein the biological compound is bilirubin.

* * * * *